United States Patent [19]
Hancock et al.

[11] 3,966,401
[45] June 29, 1976

[54] PREPARING NATURAL TISSUE FOR IMPLANTATION SO AS TO PROVIDE IMPROVED FLEXIBILITY

[75] Inventors: Warren D. Hancock, Santa Ana; Thomas J. Fogarty, Palo Alto, both of Calif.

[73] Assignee: Hancock Laboratories Incorporated, Anaheim, Calif.

[22] Filed: July 1, 1974

[21] Appl. No.: 485,159

[52] U.S. Cl. .................................. 8/94.11; 3/1; 3/1.5; 128/274
[51] Int. Cl.² ................. A61L 17/00; A63B 51/02; D01C 3/00; D01F 5/00
[58] Field of Search ............... 8/94.11; 3/1, DIG. 3; 128/274

[56] References Cited
UNITED STATES PATENTS
2,900,644  8/1959  Rosenberg ............................... 3/1

OTHER PUBLICATIONS
O'Brien et al., J. Thoracic & Cardiovascular Surgery, 1967, 53, 392–397.

Reed, J. Thoracic & Cardiovascular Surgery, 1969, 57, 663–668.

Carpentier et al., J. Thoracic & Cardiovascular Surgery, 1969, 58, 467–483.

*Primary Examiner*—Morton Foelak
*Attorney, Agent, or Firm*—Gausewitz, Carr & Rothenberg

[57] ABSTRACT

An arrangement for preparing natural tissue in the form of a heart valve, vessel or the like for implantation in which alternately tanning fluid under pressure is applied to a portion of the tissue so as to cause said tissue to assume substantially its natural configuration, and the pressure is relieved so as to result in a flexing of the tissue, while additional tanning fluid is applied to the remainder of the tissue, said tanning fluid being so applied for a time sufficient to cause the tissue to become fixed.

13 Claims, 6 Drawing Figures

U.S. Patent   June 29, 1976   3,966,401
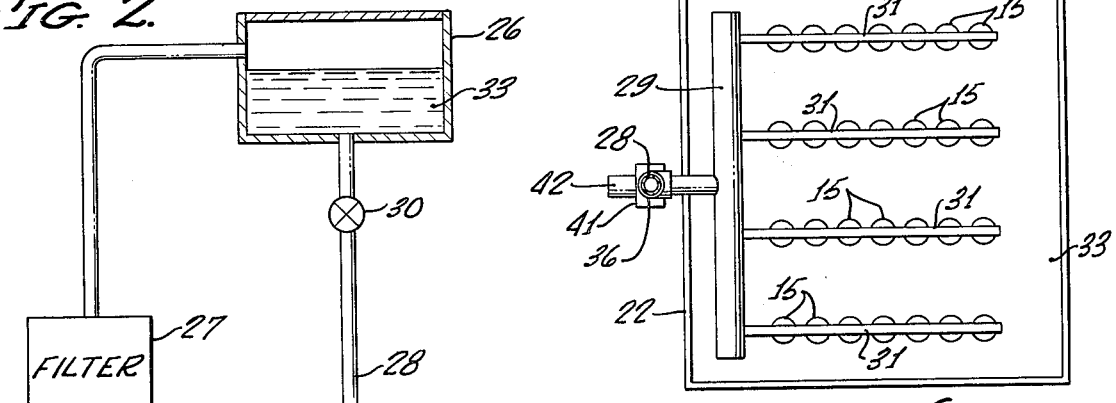
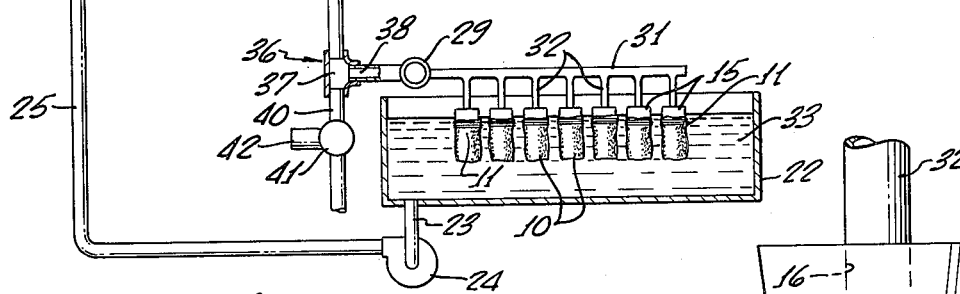
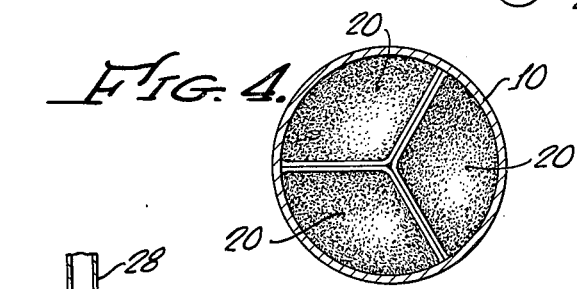
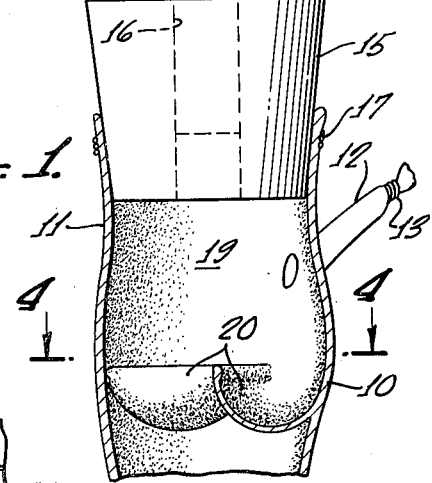
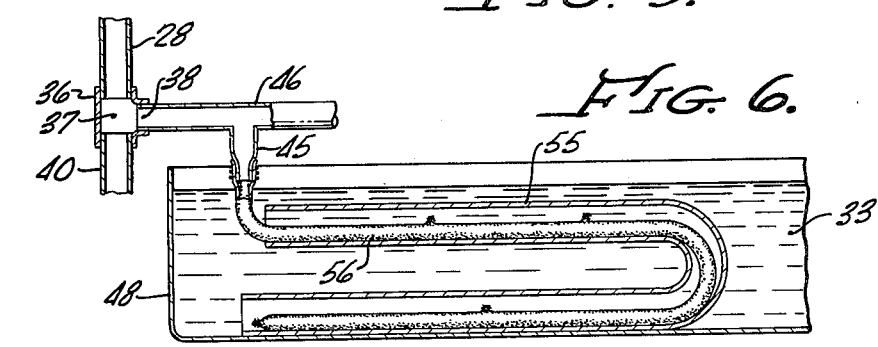

PREPARING NATURAL TISSUE FOR IMPLANTATION SO AS TO PROVIDE IMPROVED FLEXIBILITY

BACKGROUND OF THE INVENTION

1. Field of the Invention

This invention relates to the preparation of natural tissue for implantation.

2. Description of Prior Art

In the past, natural tissues in the form of heart valves, arteries, veins and the like have been prepared for implantation by subjection to a bath of tanning fluid, but have possessed serious shortcomings upon completion of the tanning process. Shape retention, strength and life of the tissues upon implantation are among the areas of deficiency for such prepared tissues.

A major improvement was effected by subjecting the tissue structure to tanning fluid under pressure to cause it to assume substantially its natural configuration during the tanning period. Such a process is described in patent application Ser. No. 324,217 for Arrangement for Preparing Natural Tissue for Implantation, filed Jan. 16, 1973, by Warren D. Hancock and Frederick P. Sattler, now abandoned, and its continuation-in-part Ser. No. 490,686, filed July 22, 1974. This resulted in improved architecture of the tissues, higher tensile strength and greater and more uniform penetration of the fixative. However, the tissues treated in this manner nevertheless were considerably more rigid than corresponding tissues in their natural state. The lack of flexibility may prevent such tissues from achieving maximum life and performance upon implantation.

SUMMARY OF THE INVENTION

The present invention provides an improved treatment for natural tissues so that they retain flexibility at the conclusion of the tanning process. According to the invention, the tissues, such as a heart valve, vessel or the like, are alternately pressurized to within the physiologic range and relieved of such pressure. The pressure is provided by tanning fluid which inflates the structure provided by the tissues to assume substantially its natural configuration. Additional tanning fluid at a lower pressure is applied to other portions of the tissues. The pulsation of pressure is continued throughout the tanning cycle, so that the tissues are flexed intermittently during this period. The result is a materially improved flexability, at the same time retaining the advantages of fixation under pressure. Tissues so prepared have a longer useful life upon implantation with greater assurance of proper functioning.

BRIEF DESCRIPTION OF THE DRAWING

FIG. 1 is a longitudinal sectional view of a valve structure attached to a device for applying pressurized tanning fluid and after being fixed by the tanning fluid;

FIG. 2 is an elevational view, partially in section, illustrating an arrangement for treating a number of valves;

FIG. 3 is a top plan view showing the manifolding arrangement for distributing the tanning fluid;

FIG. 4 is a sectional view taken along line 4—4 of FIG. 1;

FIG. 5 is a side elevational view, partially in section, illustrating the arrangement for fixing vessels for implantation; and FIG. 6 is a view similar to FIG. 5, but of a vessel received in a curved tube as a guide member, with the vessel shown unpressurized.

DESCRIPTION OF THE PREFERRED EMBODIMENT

In the example of FIGS. 1 through 4, the present invention is used in preparing heart valves for transplant. Illustrated in FIG. 1 is an aortic valve 10 which has been excised along with the ascending aorta 11 and extraneous tissue removed. This includes removal of the aorta above the sinus of the Valsalva, the annulus and subvalvular structure. The coronary arteries 12 are ligated by sutures 13. The aorta 11 then is extended around a rubber stopper 15, which has a central axially extending opening 16 through it. The stopper 15, therefore, is positioned in the aorta 11 above the valve 10, between the valve and the arch of the aorta. A suture 17 is wrapped around the exterior to affix the aorta to the stopper 15. The result is the formation of a chamber 19 within the valve structure, closed at its lower end by the cusps 20 of the valve. Access to the upper portion of the chamber 19 is provided by the opening 16 through the stopper 15. This allows pressurized tanning fluid to be introduced into the chamber 19 to inflate the valve 10 in its natural configuration.

In order to pressurize the valve, the arrangement shown in FIGS. 2 and 3 may be employed, which provides a means for treating a number of valves simultaneously. This system includes an open-topped tank 22 from the bottom of which extends a line 23 to a pump 24. The latter, through a conduit 25, connects to a reservoir 26 that is located above the tank 22. A filter 27 in the line 25 will remove any impurities in fluid conducted through the line 25 to the reservoir 26. Extending downwardly from the reservoir 26 is a line 28, the lower end of which connects to a main manifold 29. A shutoff valve 30 may be included in the line 28. Additional and smaller manifolds 31 extend outwardly from the main manifold 29, each of these being provided with a plurality of downwardly extending stems 32. The openings 16 of stoppers 15 to which valve elements have been attached receive the open lower ends of the stems 32. This positions the valve structures 10 within the tank 22.

A suitable tanning fluid 33, such as formaldehyde, glutaraldehyde or other aldehyde, is introduced into the tank 22 and the reservoir 26. The fluid 33 in the tank 22 covers the exteriors of the valve structures 10. This causes the upstream ends of the valves 10 to be submerged in the tanning fluid 33.

The fluid 33 from the reservoir 26 can enter the interior chambers 19 of the valves 10, where it is retained by the cusps 20. Because the reservoir 26 is elevated with respect to the location of the valves 10, a static pressure head is developed which causes the tanning fluid in the chambers 19 to exert pressure against each of the valves 10. This fluid pressure applied from the proximal aorta, being thus on the downstream side of the valve 10, inflates the valve and causes the valve to assume its natural contour. The maximum elevation of the fluid 33 in the reservoir 26 is kept at a height to produce a pressure head such that the valves will be pressurized within the physiologic range. This is from 80 to 120 mm Hg, with 80 mm Hg being used most frequently as the pressurizing value. The pressurization is controlled accurately and changed as needed by selecting an appropriate elevation of the reservoir 26 over the tank 22 to result in a desired pressure head.

The system also includes a means for pulsing the pressure in the chambers 19 so that it alternately is within the physiologic range and at a value below this range. This causes the valve 10 to be inflated to its natural contour intermittently.

In the example illustrated, there is a tee fitting 36 in the line 28 that leads from the reservoir 26 to the manifold 29. The tee 36 is positioned so that its straight-through passageway 37 is vertical, while its lateral passage 38 is horizontal and leads to the manifold 29. The upper end of the tee 36 receives the vertical part of the line 28 extending downwardly from the reservoir 26. At the lower end of the tee, connecting to the straight-through passageway 37, downstream of the lateral passageway 38, is a drain line 40, within which is a valve 41 automatically controlled to open and close repeatedly. Any suitable arrangement may be used for accomplishing the valve actuation, such as the motor-driven actuator 42 as indicated in FIG. 1.

With the heart valve 10 positioned in the tank 22 and subject to the application of the tanning fluid on both its interior and exterior surfaces, the valve 41 in the line 28 is continually opened and closed by the actuator 42. When the valve 41 is closed, the 80 to 120 mm Hg pressure head from the tanning fluid supply is realized within the chamber 19. This causes the heart valve 10 to expand and achieve substantially its natural pressurized configuration, as shown in FIGS. 1 and 4. When the valve 41 is opened, the tanning fluid 33 then drains directly from the tank 26 through the vertical passage 37 of the tee 36 into the drain 40. This relieves the pressure within the chamber 19. Moreover, the flow of fluid through the passageway 37 of the tee 36 creates a venturi effect, so that a negative pressure may be realized in the chamber 19. Therefore, continued operation of the valve 41 causes a pulsation of the pressure within the chamber 19, ranging from a peak pressure within the normal physiologic range to minimal pressure or even a vacuum. This cycling of the pressure within the chamber 19, which in a typical example provides a pressure pulse once each second, is continued throughout the tanning process. Complete fixation of the tissue of a heart valve in a 4% formaldehyde solution or 0.2% glutaraldehyde solution will occur in around 12 hours, but advantage is gained by continued fixation up to around 72 hours. The preferred tanning fluid is a 0.2% glutaraldehyde solution buffered to a pH of 7.4 and an osmolarity of 290 milliosmols.

The pulsation of the pressure within the chamber 19 is advantageous in flexing the valve tissue as it is fixed, resulting in considerably greater flexibility at the end of the tanning cycle. This is particularly important in assuring prolonged competence of the heart valve. Valve life is increased significantly. The advantages of applying the tanning fluid under pressure are retained as well. Thus, the valve 10 will not shrink during the tanning process and has its natural architecture when the fixation is complete. The tensile strength of the valve is increased, there is better penetration of the fixative and the penetration is more uniform than otherwise. Also, heart valves that inherently will leak may be detected by leakage through them during the tanning process so that they can be discarded.

The use of this invention is preparing arteries and veins for implantation may be seen in FIG. 5. here one end of each vessel 44 is fitted over the downwardly extending stem 45 of a fluid manifold 46, held to it by means of sutures 47. The manifold 46 may be generally similar to the manifold 31 described above. The vessel 44 is received within a shallow tank 48 containing the tanning fluid 33. The other end 49 of the vessel 44 is ligated by sutures 50, and its collaterals 51 are ligated by sutures 52. This causes the vessel 44 to define an enclosed chamber. Within the interior of the vessel 44 is a straight rod 53, which extends the major part of the length of the vessel. The rod 53 is made of a suitable inert material, such as glass or a plastic such as polyolefin, and is of a constant outside diameter. The diameter of the rod 53 is less than that the vessel 44 assumes when it is under its normal physiologic pressure. The rod, however, serves to keep the vessel 44 straight under all conditions, this being the natural configuration for the vessel illustrated.

The manifold 46 is connected to a tee fitting 36 adjacent the tank 48 from which there is a valve-controlled drain as in the previously described embodiment. The pressure within the vessel 44, therefore, is fluctuated between the physiologic range and a lesser value during the tanning cycle, which is similar in length to that for a heart valve. This continually flexes the wall of the vessel as it intermittently is inflated to its natural pressurized contour. During this time, the rod 53 acts as a guide in maintaining the vessel 44 in a straight configuration. At the end of the tanning procedure, the vessel 44 possesses the important flexibility noted above, as well as other advantages resulting from the application of pressurized tanning fluid.

A curved rod may be used to impart a special shape to a vessel as it is being fixed through the application of tanning fluid fluctuating in pressure. A tubular guide also may be used, to give a curved, straight or other configuration to the vessel as it is fixed. In FIG. 6, a curved tube 55 surrounds a vessel 56 to guide the vessel and impart a corresponding shape to it. The tube 55 has a greater internal diameter than the external lateral dimension of the vessel 56 when unpressurized, which condition is shown in FIG. 6. Upon the intermittent pressurization of the vessel 56, however, it approaches the internal dimension of the tube 55. When the tanning is complete, the vessel 56 will retain the overall contour of the tube 55, as well as possessing flexibility and the other improved properties noted above.

The foregoing detailed description is to be clearly understood as given by way of illustration and example only, the spirit and scope of this invention being limited solely by the appended claims.

What is claimed is:
1. The method of preparing for implantation natural tissues in a form in which a portion thereof is subjected to pressure within the physiologic range when implanted and which assumes a predetermined configuration as a result of such pressure comprising the steps of
    alternately applying a tanning fluid to said portion of said tissues at a pressure within the physiologic range, and relieving the pressure on said portion of said tissues to less than that of said physiologic range,
        whereby said portion of said tissues is caused to assume said predetermined configuration intermittently,
    and simultaneously applying a tanning fluid to remaining parts of said tissues at a pressure below said physiologic range so as to cause said portion and said remaining parts of said tissues to become fixed while said portion of said tissues intermittently assumes said predetermined configuration.

2. The method as recited in claim 1 in which said pressure within the physiologic range is substantially within the range of from about 80 to about 120 mm Hg.

3. The method as recited in claim 1 in which said tanning fluid is a 0.2% glutaraldehyde solution buffered to a pH of around 7.4 and an osmolarity of around 290 milliosmols.

4. The method as recited in claim 1 in which said tanning fluid is a 4% formaldehyde solution, and in which said tanning fluid is so applied to said portion and said remaining parts of said tissues for around 72 hours.

5. The method as recited in claim 1 in which said tanning fluid is a 0.2% glutaraldehyde solution, and in which said tanning fluid is so applied to said portion and said remaining parts of said tissues for around 72 hours.

6. The method as recited in claim 1 in which, for so applying said tanning fluid to said portion of said tissues at said pressure within the physiologic range, a source of said tanning fluid under pressure is provided, and a conduit is extended from said source to said portion of said tissues, for thereby so applying said tanning fluid to said portion of said tissues.

7. The method as recited in claim 5 in which, for said source of said tanning fluid under pressure, a quantity of said tanning fluid is provided at a predetermined height relative to said portion of said tissues, thereby to provide a pressure head which will produce said pressure within the physiologic range.

8. The method as recited in claim 6 in which a drain means is provided in said conduit, said drain means alternately being closed so that said tanning fluid from said source is so applied to said portion of said tissues at said pressure within the physiologic range, and being opened for so relieving the pressure on said portion of said tissues.

9. The method as recited in claim 7 in which said conduit is provided with a means defining a substantially vertical passageway, and a lateral passageway extending from said substantially vertical passageway to said portion of said tissues, said drain means is connected to said substantially vertical passageway downstream of said lateral passageway, and a valve means is provided in said drain means for causing said drain means to be so alternately closed and opened.

10. The method as recited in claim 1 in which said tissues constitute a vessel, one end and any collaterals of said vessel are closed, tanning fluid is applied to the interior of said vessel for so applying said tanning fluid to said portion of said tissues, and tanning fluid is applied to the exterior of said vessel for so applying tanning fluid to said remaining parts of said tissues.

11. The method as recited in claim 1 in which said tissues constitute a heart valve, tanning fluid is applied to the downstream end of said heart valve for so applying said tanning fluid to said portion of said tissues, and tanning fluid is applied to the upstream end of said valve for so applying said tanning fluid to said remaining parts of said tissues.

12. The method as recited in claim 1 in which said tanning fluid is so applied to said portion of said tissues at approximately one second intervals.

13. The method of preparing a natural heart valve for implantation comprising the steps of inserting a member having an aperture therethrough into the ascending aorta of a unit that includes a natural heart valve and its ascending aorta, attaching said aorta to said member so that said unit and said member define a chamber and said aperture provides access to the interior of said chamber at the downstream end of said valve.

ligating the arteries of said unit so as to close said chamber, alternately introducing a tanning fluid which is pressurized to within the physiologic range of pressure for said valve through said aperture into said chamber so as to inflate said valve and cause said valve to assume substantially its natural configuration, and relieving the pressure of such tanning fluid, thereby to cause intermittent flexing of said valve, simultaneously applying such tanning fluid at a pressure below said physiologic range of pressure to the exterior of said unit while said valve is so intermittently flexed, and maintaining said tanning fluid so applied to the exterior of said unit and continuing to so alternately introducing tanning fluid into said chamber and relieving the pressure thereof for a time sufficient to cause the tissue of said valve to become substantially fixed, thereby to cause said valve to substantially maintain said configuration while possessing flexibility.

\* \* \* \* \*